US005158544A

United States Patent [19]
Weinstein

[11] Patent Number: 5,158,544
[45] Date of Patent: Oct. 27, 1992

[54] ARTERIAL CATHETER

[76] Inventor: James D. Weinstein, 1109 Woodland Dr., Bridgeport, W. Va. 26330

[21] Appl. No.: 786,277

[22] Filed: Nov. 1, 1991

[51] Int. Cl.⁵ ............................................ A61M 5/178
[52] U.S. Cl. ...................................... 604/164; 604/53
[58] Field of Search ............... 604/164, 171, 264, 272, 604/53

[56] References Cited

U.S. PATENT DOCUMENTS

| | | | |
|---|---|---|---|
| 4,323,071 | 4/1982 | Simpson et al. | 604/53 |
| 4,417,886 | 11/1983 | Frankhouser | 604/53 |
| 4,692,142 | 9/1987 | Dignam et al. | 604/272 |
| 4,844,092 | 7/1989 | Rydell et al. | 604/164 |
| 4,894,052 | 1/1990 | Crawford | 604/53 |
| 5,064,415 | 11/1991 | Walder et al. | 604/171 |

FOREIGN PATENT DOCUMENTS 232074 8/1987 European Pat. Off. ............ 604/264

Primary Examiner—John G. Weiss
Attorney, Agent, or Firm—Reed Smith Shaw & McClay

[57] ABSTRACT

A catheter system for percutaneous insertion into the lumen of a vessel which includes a hollow introducer needle coaxially mounted within the catheter. Mounted with the introducer needle is a guide wire which is attached to the proximal end of the needle and formed in the shape of a loop of a length sufficient to provide the necessary amount of wire to guide the catheter within the lumen. The catheter has a notched tip to help maintain the tip in the vessel lumen during guide wire placement and to inhibit passing through the opposite wall of the vessel lumen during insertion of the device.

5 Claims, 1 Drawing Sheet

ARTERIAL CATHETER

FIELD OF THE INVENTION

The present invention relates to an improved arterial catheter and particularly to an arterial catheter having an introducer needle and coaxially mounted guide wire permanently affixed thereto.

BACKGROUND OF THE INVENTION

It is generally well known to utilize a small hollow needle to assist in introducing a catheter into the lumen of a blood vessel. As known in the prior art the needle is typically positioned coaxially within the catheter or cannula with its distal end projecting beyond the distal end of the catheter. To assist in feeding the catheter into the blood vessel, a guide wire is typically fed through the hollow needle and into the blood vessel after the needle has been properly positioned within the vessel. Numerous prior art devices have been proposed to facilitate the percutaneous catheterization of a blood vessel. See, for example, U.S. Pat. Nos. 4,961,729; 4,650,472; 4,772,264 and 4,655,750.

Unfortunately, many of the prior art devices do not provide a means for containing the guide wire as an integral part of the unit. These devices require that the practitioner insert the wire through the needle after it has been inserted into the blood vessel. The device shown and described in U.S. Pat. No. 4,655,750, however, discloses an integral guide wire positioned through the center plug of the introducer needle wire which is contained in a sterile bag covering the proximal end of the guide wire. U.S. Pat. No. 4,417,886 discloses a catheter mounted over an introducer needle in which the guide wire is positioned within a proximally mounted tube having a slot for guiding a wire pushing mechanism for insertion through the needle into the blood vessel.

While attempts have been made to facilitate the use of a wire guide in catheter introducer needles, these devices are both complex and relatively expensive. Accordingly, it is an object of the present invention to provide an arterial catheter system which provides a low cost, relatively simple and easy to use catheter system having an integral guide wire. It is a further an object of the invention to overcome the limitations of prior art catheter systems in a cost effective manner. It is also an object of the invention to provide a catheter having a distal means to inhibit the penetration of the catheter through the opposite wall of the vessel and reduce the tendency of the catheter to be withdrawn from the vessel lumen when the guide wire is inserted into the vessel lumen.

SUMMARY OF THE INVENTION

The present invention provides a catheter system which comprises a small diameter introducer needle for use in arterial catheterization. The introducer needle is hollow and has a sharp distal end for percutaneous insertion into a blood vessel. The needle with guide wire is mounted coaxially in a small diameter flexible catheter such that the needle's sharp end projects slightly beyond the distal tip of the catheter. The catheter is preferably provided with a small annular groove at its distal end. This annular groove is preferred so as to reduce the tendency of the needle and catheter to pass through both walls of the vessel on its insertion and inhibit the tendency of the catheter to be withdrawn from the vessel lumen as the guide wire is passed into the vessel lumen, prior to the catheter insertion.

The guide wire is integrally mounted to the introducer needle such that its distal end extends through the needle to a position adjacent to the distal end of the needle. The guide wire terminates in the formation of a loop at the proximal end of the introducer needle. The terminus of the wire is preferably mounted to the proximal end fitting of the introducer needle. Preferably, the loop of guide wire includes a sterile covering such as a plastic shrink wrapping and the length of wire forming the loop is sufficient to provide the necessary guide for the catheter.

In operation, the introducer needle is inserted and positioned within the vessel lumen. The guide wire is then directed into the vessel through the needle by asserting a slight pressure on the loop at the proximal end. After the guide wire has been inserted the catheter is directed in the vessel over the guide wire. Once positioned, the introducer needle guide wire is withdrawn, and the catheter is connected to an external means.

The present invention facilitates the percutaneous placement of a catheter within a vessel lumen by means of a low cost needle catheter assembly. Other advantages of the invention will became apparent from a perusal of the following detailed description of a presently preferred embodiment taken in connection with the accompanying drawings.

PRESENTLY PREFERRED EMBODIMENT

Figure 1:
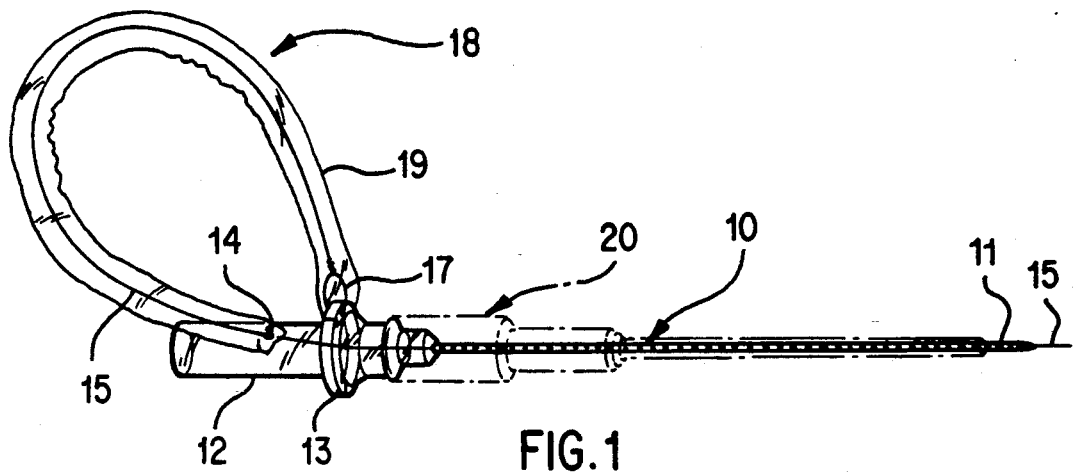
FIG. 1 is a perspective view of the introducer needle of the present invention having a guide wire integrally attached thereto.

Referring to FIG. 1, introducer needle 10 of the present invention has a distal end 11 formed with a sharp point. Needle 10 includes a luer hub assembly 12 located at its proximal end. Hub 12 preferably includes annular flange 13 with opening 14 extending from the outer surface of the hub to the center for communication with the interior of the hollow needle 10. Hub 12 is preferably made from a transparent plastic material similar to prior art needle fittings. Guide wire 15 extends from the distal end of needle 11 through hub 12 and exits hub 12 through opening 14. Guide wire 15 is a pliable spring wire of the type commonly used for this purpose in the profession and is preferably coated for example with a Teflon ® material. Terminus 17 of guide wire 15 is secured to annular flange 13 of the hub or other location on hub 12 and is formed in the shape of loop 18. Preferably, loop 18 includes a protective or sterile covering 19 thereover made from a plastic shrink wrap. The length of wire 15 comprising loop 18 is sufficient to provide enough wire in the vessel to properly guide catheter 20.

Figure 2:
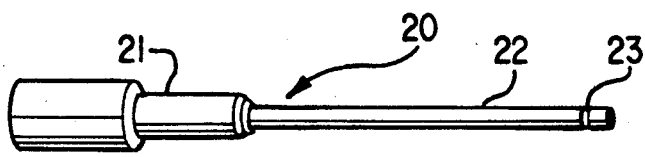
FIG. 2 is a perspective view of the catheter or of the present invention.

Referring to FIG. 2, catheter 20 includes fitting 21 adapted to fit over luer hub 12 of needle 10. Catheter 20 includes an elongated flexible catheter portion 22 at its distal end which is adapted for insertion into a lumen of a blood vessel. Preferably, distal end 22 includes annular groove 23 which is adapted to reduce the tendency of needle 10 and catheter 20 to pass through the opposite wall of the vessel with the initial insertion or to be removed from the vessel as the guide wire 15 is positioned within the vessel lumen.

Figure 3:
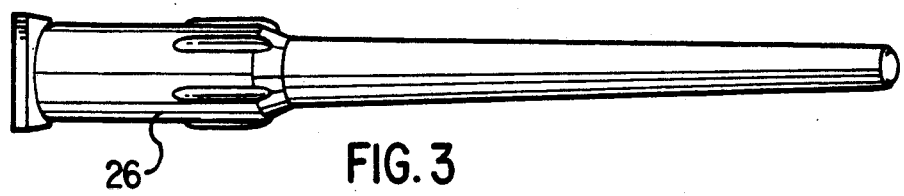
FIG. 3 is a perspective view of the catheter assembly cover.

Protective cover 26, shown in FIG. 3, receives the combined assembly of the introducer needle and catheter 20. Protective cover 26 is preferably made from a plastic material which is easily sterilizable.

Figure 4:
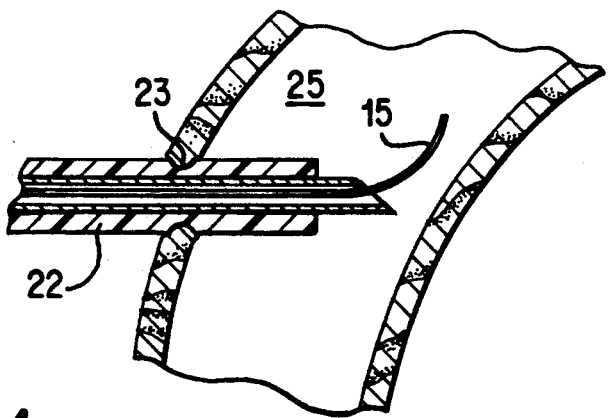
FIG. 4 is a sectional elevation showing the catheter of the presentation inserted in a vessel lumen.

In use, catheter 20 coaxially positioned over introducer needle 10 such that catheter receiving member 21 compression fits hub 12 of needle 10 as shown in dotted lines in FIG. 1. Distal end 11 of needle 10 projects slightly beyond the distal end of catheter portion 22. Guide wire 15 is located within distal end 11 of needle 10 spared slightly away from the point of the needle. Cover 26 is removed from the assembly and the distal end of needle 10 is percutaneously inserted into the lumen of a blood vessel 25, as shown in FIG. 4. When needle 10 is properly located within the lumen, guide wire 15 is inserted into the vessel by pushing on loop 18. The guide wire 15 does not fill needle 10 so blood can traverse through needle 10, which will indicate that tip of needle 10 is in vessel lumen. Guide wire 15 does inhibit blood flow. Upon placement of guide wire 15 within the vessel lumen, catheter 20 is moved along the guide wire within the vessel to properly locate catheter 20 therein. After positioning catheter 20 within the vessel, needle 10, along with guide wire 15, are removed.

While a presently preferred embodiment of the invention has been shown and described in particularity, the invention may otherwise be embodied within the scope of the appended claims.

What is claimed is:

1. A catheter system for percutaneous insertion and placement of a catheter in the lumen of a vessel comprising:
   a. a small diameter hollow introducer needle having a sharp end point at its distal end and a hub at its proximal end having an opening therein:
   b. a flexible catheter coaxially mounted over said introducer needle having a receiving fitting at its proximal end for receiving the needle hub for communication with said hollow needle; and
   c. a guide wire coaxially positioned within said introducer needle with its distal end positioned adjacent said needle point and its terminus attached to the exterior of said needle hub, said guide wire exiting the needle through said opening in said hub and forming a loop between said opening and terminus where the length of wire forming said loop is associated with the length necessary to guide said catheter in the lumen.

2. A catheter as set forth in claim 1 wherein said catheter includes an annular groove at its distal end.

3. A catheter as set forth in claim 1 wherein said guide wire loop is covered with a protective covering.

4. A catheter system as set forth in claim 1 or 2 wherein said opening in the needle hub is through a side wall thereof.

5. A catheter system as set forth in claim 1 or 2 wherein said introducer needle hub is a luer type fitting.

* * * * *